United States Patent
Li

(10) Patent No.: US 12,089,994 B2
(45) Date of Patent: Sep. 17, 2024

(54) ULTRASOUND ELASTICITY MEASURING DEVICES AND ELASTICITY COMPARATIVE MEASURING METHODS

(71) Applicant: SHENZHEN MINDRAY BIO-MEDICAL ELECTRONICS CO., LTD., Guangdong (CN)

(72) Inventor: Shuangshuang Li, Shenzhen (CN)

(73) Assignee: Shenzhen Mindray Bio-Medical Electronics Co., Ltd., Shenzhen (CN)

( * ) Notice: Subject to any disclaimer, the term of this patent is extended or adjusted under 35 U.S.C. 154(b) by 165 days.

(21) Appl. No.: 16/852,012

(22) Filed: Apr. 17, 2020

(65) Prior Publication Data

US 2020/0237343 A1 Jul. 30, 2020

Related U.S. Application Data

(63) Continuation of application No. PCT/CN2017/106897, filed on Oct. 19, 2017.

(51) Int. Cl.
*A61B 8/08* (2006.01)
*A61B 8/00* (2006.01)

(52) U.S. Cl.
CPC ............. *A61B 8/485* (2013.01); *A61B 8/463* (2013.01); *A61B 8/469* (2013.01); *A61B 8/5223* (2013.01); *A61B 8/5246* (2013.01); *A61B 8/54* (2013.01)

(58) Field of Classification Search
CPC ......... A61B 8/463; A61B 8/469; A61B 8/485; A61B 8/5223; A61B 8/5246; A61B 8/54
See application file for complete search history.

(56) References Cited

U.S. PATENT DOCUMENTS 9,044,175 B2  6/2015 Waki et al.
9,161,736 B2  10/2015 Waki
(Continued)

FOREIGN PATENT DOCUMENTS

CN  101421610 A  4/2009
CN  102469989 A  5/2012
(Continued)

OTHER PUBLICATIONS

Geer et al. (Least Squares Estimation. Encyclopedia of Statistics in Behavioral Science). (Year: 2005).*
(Continued)

*Primary Examiner* — Michael T Rozanski
(74) *Attorney, Agent, or Firm* — Sheppard Mullin Richter & Hampton LLP

(57) ABSTRACT

An elasticity comparative measuring method includes: controlling an ultrasound probe to transmit a first ultrasound wave to a region of interest in a biological tissue when the biological tissue is deformed; receiving echoes of the first ultrasound wave to obtain a first echo signal; controlling the ultrasound probe to transmit a second ultrasound wave to the region of interest when the biological tissue is deformed; receiving echoes of the second ultrasound wave to obtain a second echo signal; obtaining a first elasticity result corresponding to a first cross section in the region of interest according to the first echo signal; obtaining a second elasticity result corresponding to a second cross section in the region of interest according to the second echo signal; outputting, via a display, the first elasticity result and the second elasticity result.

14 Claims, 5 Drawing Sheets

(56) References Cited

U.S. PATENT DOCUMENTS

| | | | |
|---|---|---|---|
| 9,622,711 B2 | 4/2017 | Zhao et al. | |
| 2004/0244490 A1 | 12/2004 | Turner | |
| 2005/0015010 A1 | 1/2005 | Antich et al. | |
| 2009/0099447 A1* | 4/2009 | De Korte | G01S 15/8995 |
| | | | 600/438 |
| 2009/0216119 A1 | 8/2009 | Fan et al. | |
| 2009/0217764 A1 | 9/2009 | Kröning et al. | |
| 2012/0157831 A1 | 6/2012 | Waki | |
| 2013/0317361 A1 | 11/2013 | Tabaru et al. | |
| 2014/0343422 A1* | 11/2014 | Waki | A61B 8/483 |
| | | | 600/438 |
| 2016/0059044 A1* | 3/2016 | Gertner | A61B 90/37 |
| | | | 601/2 |
| 2017/0360408 A1* | 12/2017 | Toji | G01S 7/52022 |
| 2019/0167233 A1* | 6/2019 | Konofagou | A61B 8/486 |

FOREIGN PATENT DOCUMENTS

| | | |
|---|---|---|
| CN | 102481145 A | 5/2012 |
| CN | 102647946 A | 8/2012 |
| CN | 102920482 A | 2/2013 |
| CN | 103300891 A | 9/2013 |
| CN | 103347450 A | 10/2013 |
| CN | 103917167 A | 7/2014 |
| CN | 104605891 A | 5/2015 |
| CN | 104968278 A | 10/2015 |
| CN | 105662473 A | 6/2016 |
| CN | 106154251 A | 11/2016 |
| CN | 111449629 A | 7/2020 |

OTHER PUBLICATIONS

Gennisson et al. ("Viscoelastic and Anisotropic Mechanical Properties of in vivo Muscle Tissue Assessed by Supersonic Shear Imaging." 2010). (Year: 2010).*

PCT International Search Report and the Written Opinion mailed Jul. 13, 2018, issued in related International Application No. PCT/CN2017/106897 (10 pages).

First Search dated Sep. 24, 2020, issued in related Chinese Application No. 201780088411.2 (2 pages).

First Office Action dated Sep. 28, 2020, issued in related Chinese Application No. 201780088411.2, with English machine translation (21 pages).

PCT International Preliminary Report on Patentabiity mailed Apr. 30, 2020, issued in related International Application No. PCT/CN2017/106897, with English machine translation (11 pages).

First Search dated May 11, 2022, issued in related Chinese Application No. 202110315553.6 (2 pages).

* cited by examiner ions or in different cross sections. Therefore, when elastic imaging or measurement is performed from different angles or cross-sections, the obtained values or images may be different. The characteristics or degree of the anisotropy of the tissue may provide new information to the doctor.

ULTRASOUND ELASTICITY MEASURING DEVICES AND ELASTICITY COMPARATIVE MEASURING METHODS

CROSS REFERENCE TO RELATED APPLICATION

This application is a continuation application of International Application No. PCT/CN2017/106897, filed on Oct. 19, 2017, the contents of which is incorporated herein by reference in its entirety in the present disclosure.

TECHNICAL FIELD

The present disclosure relates to medical device, in particular to an ultrasound elasticity measuring device and an elasticity comparative measuring method.

BACKGROUND

Ultrasound elasticity imaging is one of the hot spots in clinical research in recent years. Since it mainly presents the elasticity or hardness of tissues, it has been used more and more in the auxiliary detection, discrimination of benign and malignant and evaluation of prognosis recovery, etc. of the tissue cancer lesions.

The ultrasound elasticity imaging mainly images elasticity-related parameters in the region of interest, thereby presenting the hardness of the tissue. In the past two decades, many different elasticity imaging methods have been developed, such as the quasi-static elasticity imaging based on strain caused by the probe pressing the tissue, the elasticity imaging or elastic measurement based on the shear waves generated by an acoustic radiation force, and the transient elasticity imaging based on the shear waves generated by an external vibration, etc.

These elasticity imaging methods are all performed on the assumption that the target tissue is an isotropic medium. There are many types of human tissues, whose structures are complex and diverse. Most human tissues can be approximated as isotropic elastic media, that is, the elastic characteristics in different directions are the same. However, some human tissues, such as muscles, have very strong anisotropic characteristics, and the elasticity varies greatly in different directions or in different cross sections. Therefore, when elastic imaging or measurement is performed from different angles or cross-sections, the obtained values or images may be different. The characteristics or degree of the anisotropy of the tissue may provide new information to the doctor.

SUMMARY

The present disclosure provides an ultrasound elasticity measuring device and an elasticity comparative measuring method, which can measure the anisotropy parameters of biological tissue through the ultrasound elasticity measuring device.

In one embodiment, an ultrasound elasticity measuring device is provided, which may include:
- an ultrasound probe including at least one transducer, where a first part of the transducers is configured to transmit ultrasound waves for detecting an elasticity of a region of interest to the region of interest to form ultrasound waves propagating in at least two different cross sections in the region of interest, and a second part of the transducers is configured to receive ultrasound echoes reflected from a biological tissue, where the ultrasound echoes includes ultrasound echoes from the at least two different cross sections in the region of interest;
- a transmitting/receiving sequence control module configured to generate a transmitting sequence which controls transducers to transmit the ultrasound waves and a receiving sequence which controls transducers to receive the ultrasound echoes;
- an echo processing module configured to process the ultrasound echoes;
- a transmitting/receiving module which is electrically connected with the ultrasound probe, the transmitting/receiving sequence control module and the echo processing module and configured to transfer the transmitting sequence generated by the transmitting/receiving sequence control module to the ultrasound probe and transfer the ultrasound echoes received by the ultrasound probe to the echo processing module; and
- a data processing module which is connected with the echo processing module and configured to calculate elasticity results corresponding to the at least two different cross sections according to the ultrasound echoes from the at least two different cross sections.

In one embodiment, an elasticity comparative measuring method is provided, which may include:
- controlling an ultrasound probe to transmit a first ultrasound wave to a region of interest when a biological tissue is deformed;
- receiving echoes of the first ultrasound wave to obtain a first echo signal;
- controlling the ultrasound probe to transmit a second ultrasound wave to the region of interest when the biological tissue is deformed;
- receiving echoes of the second ultrasound wave to obtain a second echo signal;
- obtaining a first elasticity result corresponding to a first cross section in the region of interest according to the first echo signal;
- obtaining a second elasticity result corresponding to a second cross section in the region of interest according to the second echo signal, wherein the first cross section is different from the second cross section;
- outputting the first elasticity result and the second elasticity result.

In one embodiment, an elasticity comparative measuring method is provided, which may include:
- forming a first cross section in a region of interest, and calculating a first elasticity result corresponding to the region of interest according to the first cross section;
- forming a second cross section in the region of interest, and calculating a second elasticity result corresponding to the region of interest according to the second cross section;
- calculating an anisotropy parameter of the region of interest according to the first elasticity result and the second elasticity result;
- in response to calculations of the elasticity result, performing at least one of:
  (1) outputting a first elasticity distribution map according to the first elasticity result, and outputting a second elasticity distribution map according to the second elasticity result; and
  (2) outputting an anisotropy parameter according to the first elasticity result and the second elasticity result.

In one embodiment, an ultrasound elasticity measuring device is provided, which may include:

an ultrasound probe comprising at least one transducer, wherein a first part of the transducers is configured to transmit ultrasound waves for detecting an elasticity of a region of interest to the region of interest to form ultrasound waves propagating in at least two different cross sections in the region of interest, and a second part of the transducers is configured to receive ultrasound echoes reflected from a biological tissue, wherein the ultrasound echoes comprises ultrasound echoes from the at least two different cross sections in the region of interest;

a transmitting/receiving module which is electrically connected with the ultrasound probe and configured to: control the ultrasound probe to transmit a first ultrasound wave to the region of interest when the biological tissue is deformed and receive echoes of the first ultrasound wave to obtain a first echo signal; and control the ultrasound probe to transmit a second ultrasound wave to the region of interest when the biological tissue is deformed and receive echoes of the first ultrasound wave to obtain a second echo signal;

a data processing module configured to obtain a first elasticity result corresponding to a first cross section in the region of interest according to the first echo signal and obtain a second elasticity result corresponding to a second cross section different from the first cross section in the region of interest according to the second echo signal, and output the first elasticity result and the second elasticity result.

In one embodiment, an ultrasound elasticity measuring device is provided, which may include:

an ultrasound probe comprising at least one transducer, wherein the transducer is configured to transmit ultrasound waves to a region of interest to form a first cross section and a second cross section in the same region of interest; and a data processing module configured to calculate a first elasticity result corresponding to the region of interest according to the first cross section, calculate a second elasticity result corresponding to the region of interest according to the second cross section, calculate an anisotropy parameter of the region of interest according to the first elasticity result and the second elasticity result, and, in response to calculations of the elasticity results, performing at least one of:

(1) outputting a first elasticity distribution map according to the first elasticity result, and outputting a second elasticity distribution map according to the second elasticity result; and (2) outputting an anisotropy parameter according to the first elasticity result and the second elasticity result.

In the embodiments of the present disclosure, the detected elasticity parameters are used to calculate the anisotropy parameters of the region of interest to measure the degree of anisotropy of the region of interest, which then are output, thereby providing more reference information to the doctor for diagnosing the lesion or evaluating the clinical prognosis.

DETAILED DESCRIPTION

Figure 1:
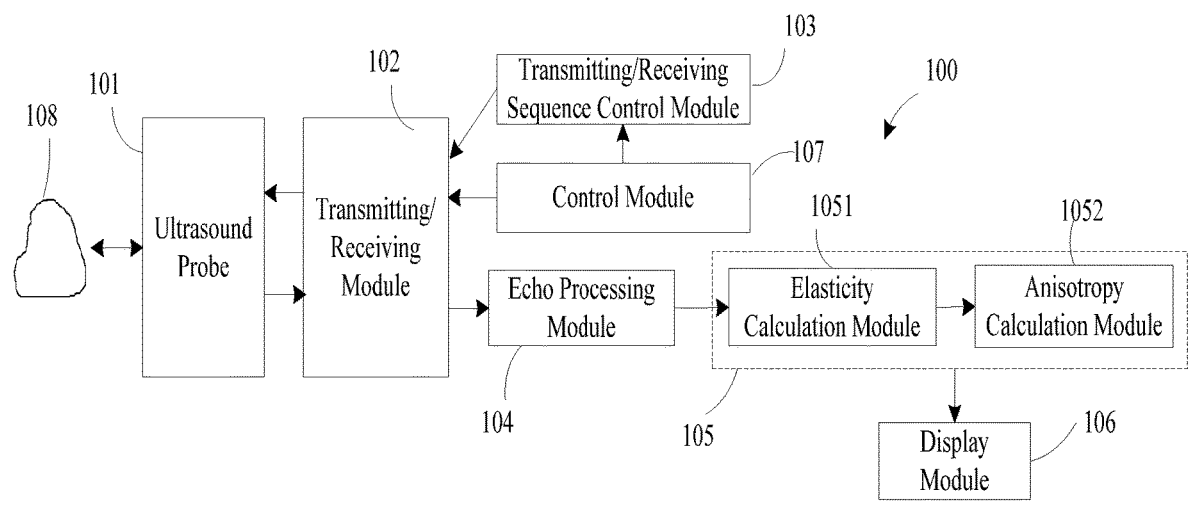
FIG. 1 is a schematic structural diagram of an ultrasound elasticity measuring device.

The present disclosure will be described in detail below with reference to the embodiments and drawings, where similar elements in different embodiments are designated with similar reference numbers. In the following embodiments, many details are described so as to facilitate the understanding to the present disclosure. However, those skilled in the art will easily recognize that some of the features may be omitted in different situations, or may be replaced by other elements, materials or methods. In some cases, some operations are not shown or described in the specification, which is to avoid the core part of the present disclosure being overwhelmed by too many descriptions. For those skilled in the art, detailed description of these operations is not necessary. They can fully understand these operations according to the description in the specification and general technical knowledge in the field.

In addition, the features, operations or characteristics described in the specification may be combined in any appropriate manner to form various embodiments. Furthermore, the steps or actions in the described methods may also be changed or adjusted in the order in a manner obvious to those skilled in the art. Therefore, the various orders in the description and drawings are only for clearly describing a certain embodiment, but not meant to be a necessary order unless otherwise stated that a certain order must be followed.

The serial numbers for the elements in the present disclosure, such as "first", "second", etc., are only used to distinguish the described objects, but do not have any order or technical meaning. The "connection" and "coupling" as used herein, unless otherwise specified, will include both direct and indirect connection (coupling).

In the embodiments of the present disclosure, the elasticity parameters of different cross sections of the region of interest of the biological tissue may be measured by an ultrasound device, and the anisotropy parameters of the region of interest may be calculated according to the elasticity parameters of the different cross sections. The anisotropy parameters may be used to represent the degree of the anisotropy of a certain tissue. The anisotropy may mean that the characteristics of the tissue change with the change of direction, showing different properties in different directions. Therefore, the anisotropy parameter may represent the different properties in different directions of the biological tissue (for example, the biological tissue may be an anatomical structure of a human or animal, such as the heart, the muscles or the blood vessels, etc.) which will change with the change of the direction. In the present disclosure, the anisotropy parameter may include the ratio of the characteristics in at least two directions, the difference between the characteristics in at least two directions, or the square of the ratio of the characteristics in at least two directions, etc. Alternatively, the anisotropy parameter may also be a secondary statistics of the obtained characteristics in at least two directions. The detailed description will be provided below, in which the characteristics are obtained by the elasticity measurement in the ultrasound device.

In the present embodiment, the anisotropy parameter may include a comparative analysis result of multiple elasticity parameters obtained in different cross sections, such as a ratio between the multiple elasticity parameters, a difference between the multiple elasticity parameters, a proportion between the multiple elasticity parameters or other secondary statistics. In the present disclosure, the ultrasound device is referred to as an ultrasound elasticity measuring device. However, those skilled in the art should understand that the ultrasound device may also have with other functions, such as performing general ultrasound diagnosis, generating B-mode ultrasound images, C-mode ultrasound image or Doppler ultrasound images, and so on.

The elasticity measurement method herein may be one or a combination of the vibration elasticity measurement based on an external vibration, the shear wave measurement based on acoustic radiation force and the strain elasticity measurement.

Specifically, in the vibration elasticity measurement based on the external vibration, an external force may be used to generate a shear wave which propagates into the tissue. The propagation of the shear waves in the biological tissue may be detected to obtain its propagation parameters (such as the propagation velocity) to represent the difference in hardness between the tissues. For an isotropic elastic tissue, there is the following relationship between the propagation velocity $C_s$ of the shear waves and the elastic modulus E of the tissue: Young's modulus $E=3\rho C_s^2$ (where, $\rho$ is the density of the tissue). In other words, there is a one-to-one correspondence between the shear wave velocity and the elastic modulus.

In the shear wave measurement based on the acoustic radiation force, the shear wave may be generate in the biological tissue by the ultrasound acoustic radiation force, and the propagation of the shear wave in the biological tissue may be detected to obtain its propagation parameters (such as the propagation velocity) to represent the difference in hardness between the biological tissues. For an isotropic elastic tissue, there is the following relationship between the propagation velocity $C_s$ of the shear waves and the elastic modulus E of the tissue: Young's modulus $E=3\rho C_s^2$ (where, $\rho$ is the density of the tissue). In other words, there is a one-to-one correspondence between the shear wave velocity and the elastic modulus.

In the strain elasticity measurement, which may also be referred to as conventional ultrasound elasticity measurement, the probe may be used to slightly press the target biological tissue or a certain pressure may be generated on the tissue through the breathing, the vascular pulsation or other processes of the human body itself, and two frames of ultrasound echo signals before and after the compression may be obtained. When the biological tissue is compressed, a strain along the compression direction will be generated in the biological tissue. If the Young's modulus distribution within the biological tissue is not uniform, the strain distribution within the biological tissue will also be different. The strain information of the biological tissue may be detected with certain methods, and the parameters related to the tissue elasticity may be calculated and outputted, such as the strain, the strain rate, etc., so as to indirectly represent the differences in the elasticity between different tissues in the pressed area. Specifically, according to Hooke's law, for an isotropic elastomer, the stress $\sigma$=the strain $\varepsilon\times$ Young's modulus E, i.e. $E=\sigma/\varepsilon$. Young's modulus E is a parameter related to tissue hardness. The higher the Young's modulus, the greater the tissue hardness. The ultrasound probe deforms the biological tissue by pressing so as to detect the elasticity in the region of interest, and the obtained elasticity result is the quasi-static elasticity parameter of the region of interest. The quasi-static elasticity parameter may be the strain or strain rate.

It should be noted that, in the present embodiment, the elasticity measurement will not be limited to those listed above. Other elasticity measurement methods based on ultrasound elasticity imaging may also be used.

Referring to FIG. 1, the ultrasound elasticity measurement device 100 may include an ultrasound probe 101, a transmission/receiving sequence control module 102, a transmitting/receiving module 103, an echo processing module 104, a data processing module 105, and a display module 106. The transmitting/receiving sequence control module 102 may be connected with the ultrasound probe 101 through the transmitting/receiving module 103, and the ultrasound probe 101 may be connected with the echo processing module 104 through the transmitting/receiving module 103. The output end of the echo processing module 104 may be connected with the data processing module 105. The output end of the data processing module 105 may be connected with the display module 106.

The ultrasound probe 101 may include at least one transducer. The transducer may be used to transmit ultrasound waves according to electrical signals or convert the received ultrasound waves into electrical signals. Multiple transducers may be arranged in a row, such as a linear probe. Alternatively, the multiple transducers may be arranged in a two-dimensional matrix, such as a two-dimensional ultrasound probe or matrix probe. A part of the transducers of the ultrasound probe 101 may be used to transmit ultrasound waves to the biological tissue 108, and another part of the transducers may be used to receive the ultrasound echoes returned from the biological tissue.

Figure 2:
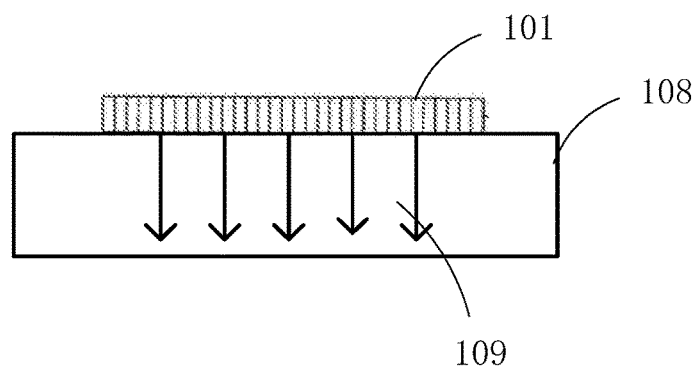
FIG. 2 is a schematic view of a cross section.

The transmitting/receiving sequence control module 102 may be configured to generate a transmitting sequence and a receiving sequence according to the instructions of the control module 107. The transmitting sequence may provide the number of transducers used in the transmitting in the ultrasound probe 101 and the parameters (such as amplitude, frequency, number of transmitting, transmitting angle, wave type, etc.) of the ultrasound waves to be transmitted to the biological tissue. The receiving sequence may provide the number of transducers used in the receiving in the ultrasound probe 101 and the parameters for receiving the echoes (such as receiving angle, depth, etc.). The transmitting sequence and the receiving sequence will be different for different purposes or different images to be generated. As shown in FIG. 2, after the ultrasound probe 101 is attached at a certain position on the biological tissue 108, the corresponding transducers in the ultrasound probe 101 may transmit ultrasound waves with a certain amplitude, frequency, and angle into the biological tissue 108 according to the transmitting sequence. The ultrasound waves may propagate in a cross section 109 in the biological tissue 108, and the echoes from this cross section may be received. In the embodiments of the present disclosure, the user may manually change the direction or position of the ultrasound probe 101 to scan different cross sections. Alternatively, the transducer may be automatically adjusted to scan different cross sections, which will be described in detail later.

The transmitting/receiving module 103 may be connected between the ultrasound probe and the transmitting/receiving sequence control module 102 and the echo processing module 104, and may be configured to transfer the transmitting sequence of the transmitting/receiving sequence control module 102 to the ultrasound probe 101 under the control of the control module 107 and transfer the ultrasound echo signals received by the ultrasound probe 101 to the echo processing module 104.

The echo processing module 104 may be configured to process the ultrasound echo signals, such as filtering, amplifying, beam forming or other processing.

The data processing module 105 may be configured to receive the echo signals processed by the echo processing module 104, and obtain desired parameters or images according to the echo signals using certain algorithms.

In the present embodiment, the data processing module 105 may include an elasticity calculation module 1051, and further include an anisotropy calculation module 1052. The elasticity calculation module 1051 may be configured to calculate the elasticity results corresponding to at least two different cross sections according to the ultrasound echo signals of the at least two different cross sections, and further generate various elasticity distribution image data or various charts or graphs according to the elasticity results. The anisotropy calculation module 1052 may be configured to calculate the anisotropy parameter of the biological tissue or of a certain region of interest in the biological tissue according to at least two elasticity results. The region of interest herein may be part or all of the biological tissue. The region of interest may be automatically generated by the system, or be obtained based on the user's selection on the ultrasound image. In one embodiment, the data processing module may also be configured to generate the ultrasound image data according to the ultrasound echo signals and output the ultrasound image data to the display module for display. The region of interest may be selected by the user on the ultrasound image.

The display module 106 may serve as an output module. The display module 106 may receive various visualization data outputted by the data processing module 105 and display various images, graphs, charts, text or data on the display interface, including anisotropy parameters and/or various elasticity image. In some embodiments, after calculating the elasticity results corresponding to the cross sections, the data processing module 105 may directly output the calculated elasticity results to the display module for display, and the user may compare the degree of anisotropy in the region of interest by himself according to the elasticity results of different cross sections. In other embodiments, the output module may also be an audio playback module, which may play the audio signal outputted by the data processing module 105 by sound. In some embodiments, the display module may be a touch screen or multiple displays, etc. In some embodiments, the output module may, in response to the calculated elasticity results, perform at least one of:

(1) outputting at least two elasticity distribution maps according to the elasticity results corresponding to the cross sections; and (2) outputting the anisotropy parameters of the region of interest according to the elasticity results corresponding to cross sections.

The different cross sections above may be the cross sections in the region of interest which are parallel to or intersect with each other.

The elasticity results used for calculating the anisotropy parameter of the tissue may be the elasticity parameter obtained during the detection of the strain of the biological tissue, or the elasticity parameter obtained during the detection of the shear wave. The detailed description will be provided below with different embodiments.

Figure 3:
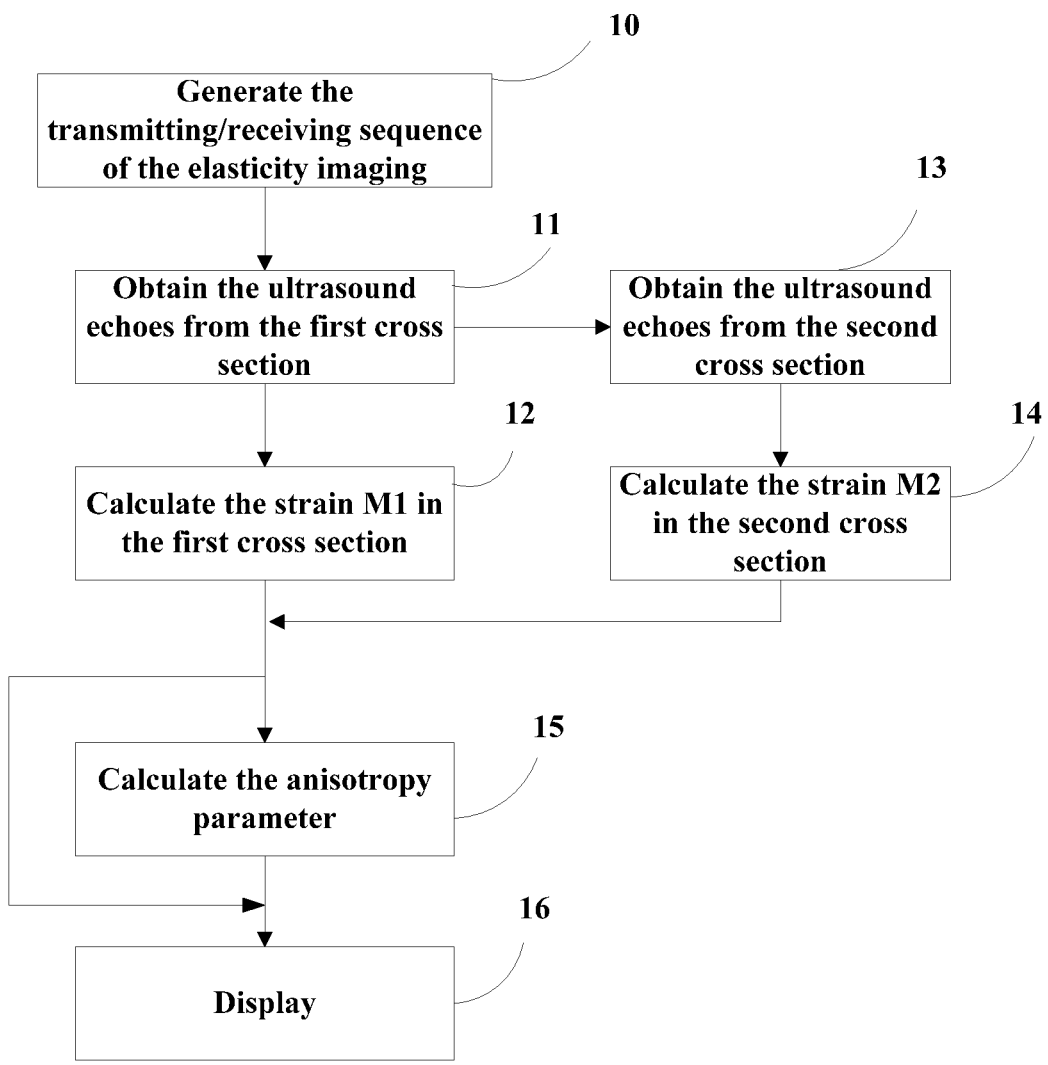
FIG. 3 is a flowchart for calculating the anisotropy parameters in one embodiment.

In one embodiment, the ultrasound elasticity measuring device 100 may detect the strain of two different cross sections in the region of interest of the biological tissue, and calculate the anisotropy parameter of the region of interest according to the strain. The processing flow is as shown in FIG. 3, which may include the following steps.

In step 10, the biological tissue may be deformed at the first position. When the user places the ultrasound probe on the biological tissue, the first position of the biological tissue may be pressed along the axial direction of the probe by manually pressing the tissue with the probe or vibrating the probe with a vibrator, so as to deform the biological tissue.

In step 11, a first transmitting and receiving sequence may be generated to control the ultrasound probe to transmit a first ultrasound wave to the biological tissue and receive the echoes of the first ultrasound wave to obtain a first echo signal.

In the present embodiment, the method for measuring the elasticity by deforming the biological tissue may be the strain elasticity measurement method and/or the vibration elasticity measurement method based on external vibration mentioned above.

The transmitting/receiving sequence control module may control the ultrasound probe to transmit the first ultrasound wave to the region of interest in the biological tissue. The first ultrasound wave may propagate in the biological tissue in a first direction, in a first cross section in the region of interest. The ultrasound echoes from the first section may be received to obtain the first echo signal. According to the first echo signal, information at multiple location points of the biological tissue on the first cross section may be obtained.

The region of interest may be selected by the user. For example, when an ultrasound image is displayed on the display screen, the user may select the region of interest on the ultrasound image, and the ultrasound elasticity measuring device may generate the transmitting and receiving sequences according to the selected region of interest. In some embodiments, the ultrasound elasticity measuring device may default that a preset area under the tissue surface contacted by the probe is the region of interest.

In step 12, a first elasticity result corresponding to the first cross section in the region of interest may be calculated according to the first ultrasound echo signal of the cross section. The first elasticity result may be the strain M1 of the region of interest in the first cross section.

Figure 4:
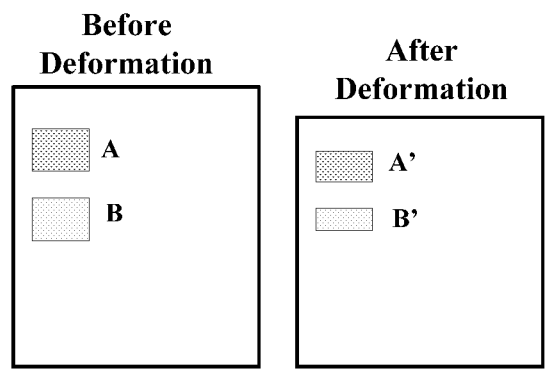
FIG. 4 is a schematic diagram of the displacement detection in the strain elasticity imaging.

The data processing module may determine the position of the region of interest after the tissue is deformed according to the two frames of ultrasound echo data before and after the tissue is deformed. There may be many displacement calculation methods. A common method may be the block-matching method. As shown in FIG. 4, for the two frames of echo data before and after the deformation, the data A, B of a certain region of interest may be selected in one frame of echo data, and the positions A', B' which most match the data A, B may be searched in the other frame of echo data. It may be considered that the region of interest is moved to the positions A', B', and the position difference between the two frames may be the displacement of the region of interest.

After the displacement data is obtained, the strain M of the region of interest may be calculated according to the definition of strain, namely:

$$M = \Delta L / L$$

Where L is the length of the region of interest before the tissue is deformed, and ΔL is the amount of change in the length of the region of interest after the tissue is deformed.

In some embodiments, a first elasticity distribution image may be obtained according to the strain M1.

In step 13, when the biological tissue is deformed, a second transmitting and receiving sequence may be generated to control the ultrasound probe to transmit a second ultrasound wave to the region of interest and receive the echoes of the second ultrasound wave to obtain a second echo signal. The deformation of the biological tissue here may be at the first position or at a second position different from the first position. In one embodiment, when the user places the ultrasound probe on the biological tissue, the second position of the biological tissue may be pressed along a direction deflected from the axis direction of the probe by manually pressing the probe or the vibrating the probe with a vibrator, so as to deform the biological tissue. The transmitting/receiving sequence control module may control the ultrasound probe to transmit the second ultrasound wave to the region of interest of the biological tissue. The second ultrasound wave may propagate in a second direction within the biological tissue, in a second cross section in the region of interest. The ultrasound echoes from the second cross section may be received to obtain the second echo signal. According to the second echo signal, information at multiple location points of biological tissue on the second cross section may be obtained.

In step 14, according to the second echo signal, a second elasticity result corresponding to the second cross section in the region of interest may be calculated, where the first cross section is different from the second cross section. In one embodiment, the second elasticity result may be the strain M2 in the region of interest in the second cross section.

Figure 5:
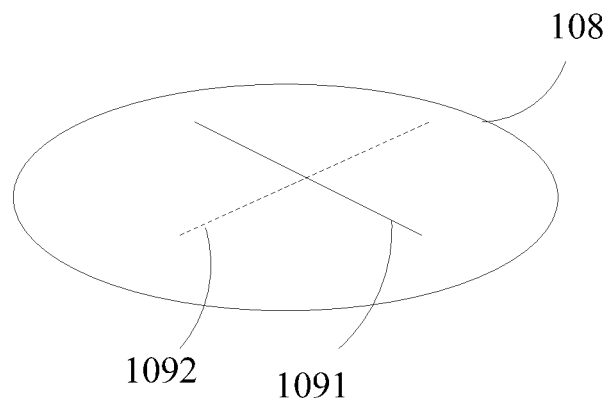
FIG. 5 is a schematic diagram of the distribution of different cross sections.
Figure 6:
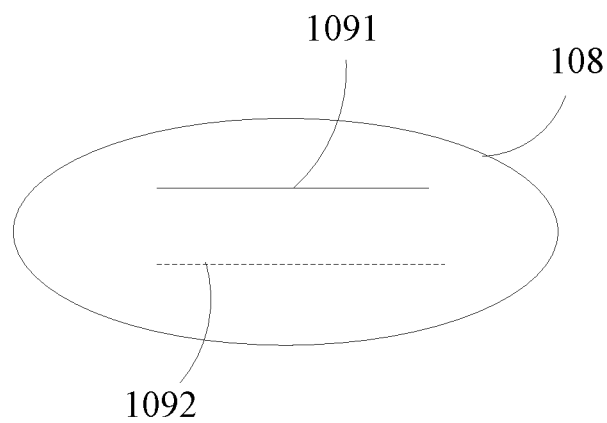
FIG. 6 is another schematic diagram of the distribution of different cross sections.

In FIG. 5, the closed area may represent the biological tissue 108, the solid line may represent the first cross section 1091, and the dotted line may represent the second cross section 1092. In the embodiment shown in FIG. 5, the first cross section 1091 and the second cross section 1092 intersect with each other. In other embodiments, as shown in FIG. 6, the first cross section 1091 and the second cross section 1092 may also be parallel to each other. For muscle tissue, one of the first cross section and second cross section may be a cross section along the direction of muscle fibers, and the other may be a cross section perpendicular to the direction of muscle fibers.

In one example, the cross section may be determined by the position and orientation of the ultrasound probe. In the present disclosure, the position of the ultrasound probe may be the placement position of the ultrasound probe on the surface of the biological body, and the orientation of the ultrasound probe may be the spatial orientation of the ultrasound probe with respect to the surface of the biological body. By changing the placement position or the spatial orientation of the ultrasound probe, the ultrasound waves for detecting the elasticity in the region of interest transmitted to such region of interest by the ultrasound probe may propagate in two different cross sections, and therefore the elasticity of the same region of interest in at least two cross section may be obtained.

In the case that the transducers of the ultrasound probe are arranged in one dimension, when it is needed to change the cross section, the user needs to manually adjust the position and/or orientation of the ultrasound probe (hereinafter referred to as manual adjustment). When the user adjusts the ultrasound probe to the first position on the biological tissue, the biological tissue may be deformed by pressing the biological tissue along the axial direction of the probe by pressing the probe manually or by vibrating the probe with a vibrator, and the transmitting/receiving sequence control module may control the ultrasound probe to transmit the ultrasound waves which will propagate in the first cross section in the region of interest to the region of interest in the biological tissue. The ultrasound probe may receive the ultrasound echoes from the first cross section to obtain the first ultrasound echo signal. In addition, when the position and/or orientation of the ultrasound probe is adjusted by the user or the system to the second position on the biological tissue different from the first position, the biological tissue may be deformed by pressing the biological tissue along the axial direction of the probe by pressing the probe manually or by vibrating the probe with a vibrator, and the transmitting/receiving sequence control module may control the ultrasound probe to transmit the ultrasound waves which will propagate in the second cross section in the region of interest to the region of interest in the biological tissue. The ultrasound probe may receive the ultrasound echoes from the second cross section to obtain the second ultrasound echo signal.

In other embodiments, in the case that the transducers of the ultrasound probe are arranged in a two-dimensional matrix, that is, the ultrasound probe is a matrix probe, the cross section may be changed by manually adjusting the position and/or orientation of the ultrasound probe by the user, as described above. Alternatively, it may also be possible to adjust the transmitting direction of the ultrasound waves or the direction of the transmitting plane by controlling the time delay, so as to obtain ultrasound waves propagating in at least two cross sections in the same region of interest. For example, the ultrasound transmitting direction or the transmitting plane may be adjusted by the transmitting/receiving sequence so as to change the cross section (hereinafter referred to as automatic adjustment). For example, the transducers and/or transmitting direction different from those of the first cross section may be determined by the transmitting sequence, so as to obtain the ultrasound waves propagating in the second cross section different from the first section. In this case, the ultrasound waves propagating in the first cross section and the second cross section may be generated during the same pressing of the probe. Alternatively, the ultrasound waves propagating in the first cross section and the second cross section may be respectively generated during the two successive pressings of the probe. For the two-dimensional matrix ultrasound probe, the user may also manually adjust the position or orientation of the ultrasound probe to change the cross section, so that ultrasound waves propagating in the first cross section and the second cross section may be formed successively, and the ultrasound echoes from the first cross section and the second cross section may be received successively. For the aforementioned automatic adjustment, it may be understood as that the ultrasound probe transmits ultrasound waves for detecting the elasticity of the region of interest to the same region of interest in different transmitting directions or transmitting planes through the control of the transmitting sequence, thereby generating ultrasound waves propagating in at least two different cross sections.

In other embodiments, the automatic adjustment may be achieved by the matrix probe. For example, at least two transducer groups may be select from the transducers in the matrix probe, which have different spatial arrangement. The at least two transducer groups may be configured to transmit ultrasound waves respectively in at least two transmitting directions or transmitting planes to the region of interest in the biological tissue, thereby obtaining the ultrasound waves propagating in at least two different cross sections.

In one embodiment, the at least two different cross sections mentioned herein may intersect with each other within the biological tissue or the region of interest. That is, the ultrasound wave transmitting directions or the ultrasound wave transmitting planes in the biological tissue may intersect with each other. In order to achieve the intersecting of the ultrasound wave transmitting directions or transmitting planes, for the linear probe, the methods described above may be used, in which it may be achieved by adjusting the placement position of the ultrasound probe on biological tissue; for the matrix probe, in addition to adjusting the placement position, the following methods may also be used. The ultrasound probe may be configured to transmit the first ultrasound wave in the first transmitting direction to the region of interest, and transmit the second ultrasound wave in the second transmitting direction to the region of interest, where the first transmitting direction may intersect with the second transmitting direction. The first ultrasound wave and the second ultrasound wave may be separately transmitted through different transducer groups, and the different transducer groups may have different spatial arrangement. There may also be overlapped portion between the transducer groups. In the present embodiment, the deformation of the biological tissue may be generated by one or a combination of the vibration generated by the external force, the ultrasound acoustic radiation force and the pressing with the ultrasound probe. The transmitting direction may be measured by the angle between the scanning plane formed by the ultrasound waves transmitted from the ultrasound probe and the surface of the ultrasound probe. Different transducer groups may have different spatial arrangements, and therefore have different transmitting directions, thereby forming different ultrasound wave transmitting planes. Therefore, the ultrasound probe may generate shear waves propagating in at least two different directions in the same region of interest in the biological tissue, and transmit ultrasound waves for detecting the shear waves, thereby obtaining the ultrasound waves propagating in at least two different cross sections. The ultrasound probe may change the spatial position of the transducer group used for transmitting the ultrasound waves to transmit the ultrasound waves for detecting the elasticity of the region of interest in different transmitting directions or transmitting planes to the same region of interest, thereby obtaining the ultrasound waves propagating in at least two different cross sections to obtain at least two elasticity results corresponding to different cross sections.

The strain M2 in the region of interest in the second cross section may be calculated according to the ultrasound echo signal of the second cross section, thereby obtaining the second elasticity calculation result corresponding to the second cross section. When the ultrasound echo signals of the second cross section are received, the strain M2 of the region of interest in the second cross section may be calculated using the same method as step 12.

The first elasticity result and the second elasticity result calculated respectively according to the first echo signal and the second echo signal may be output. In step 16, the elasticity results may be displayed through the display module. For example, in some embodiments, the data processing module may perform at least one of the following in response to the calculation of the elasticity results:

(1) outputting a first elasticity distribution map according to the first elasticity result, and outputting a second elasticity distribution map according to the second elasticity result; and (2) output the anisotropy parameter according to the first elasticity result and the second elasticity result.

The elastic distribution map may be outputted according to the elasticity results. For example, the elasticity results corresponding to the location points in the biological tissue may be obtained according to the ultrasound echo signals, and be mapped to the spatial distribution of the location points or to a single coordinate system to form the elasticity distribution map. In one embodiment, the ultrasound probe may deform the biological tissue by pressing the biological tissue to detect the elasticity of the region of interest. The elasticity result obtained thereby is a quasi-static elasticity parameter of the region of interest. The quasi-static elasticity parameter may be the strain or strain rate. The data processing module may also generate elasticity imaging data according to quasi-static elasticity parameters.

In some embodiments, in step 15, the anisotropy parameter may be further calculated. The anisotropy parameter may include the secondary statistics based on the first elasticity result and the second elasticity result. For example, the anisotropy parameter may at least include one of the ratio of the first elasticity result and the second elasticity result, the difference between the first elasticity result and the second elasticity result and a function of the ratio of or difference between the first elasticity result and the second elasticity result, etc. The function of the ratio of or difference between the first elasticity result and the second elasticity result may be the square or third power of the ratio or difference, etc.

For example, the data processing module may calculate the anisotropy parameter according to the strain M1 of the region of interest in the first cross section and the strain M2 of the region of interest in the second cross section. The anisotropy parameter may be the difference between or ratio of M1 and M2, and may also be other functions of the difference or the ratio.

In step 16, the first elasticity result and the second elasticity result obtained according to the first echo signal and the second echo signal may be output. For example, the results may be displayed. The data processing module may process the elasticity results into visual data and send the visual data to the display module for display. They may be displayed as numbers or texts, or as graphs such as column charts, pie charts and line charts, etc.

In some embodiments, the data processing module may also generate strain elasticity image data according to the strain of the region of interest in the cross sections, and display the elasticity image on the display interface. The anisotropy parameters of the region of interest may also be displayed simultaneously.

In some embodiments, the data processing module may further calculate the strain rate of the region of interest in different cross sections, and may further calculate the anisotropy parameter of the region of interest according to the strain rate of the region of interest in different cross sections.

Since the pressure for pressing the biological tissue in the present embodiment is generated manually or by a vibrator, uneven pressure may occur. Therefore, in an improved embodiment, the ultrasound elasticity measuring device may further include a pressure sensor, which may be installed in the ultrasound probe and configured to sense the pressing pressure and feed back the sensed pressure to the data processing module. The data processing module may normalize the strains detected at different times according to the pressure. For example, at time t1, the corresponding strain is S1, and the pressure is about F1; and at time t2, the corresponding strain is S2, and the pressure is about F2; then the strain result at time t2 may be normalized as S2_new=S2*F1/F2.

Generally, the elasticity imaging based on the strain of the biological tissue is called quasi-static elasticity imaging. In the present embodiment, the elasticity parameters detected during the quasi-static elasticity imaging are called quasi-static elasticity parameters, and the strain is one of the quasi-static elasticity parameters. Those skilled in the art should understand that when calculating the anisotropy parameters of the tissue, other quasi-static elasticity parameters may also be used. For example, according to the length change ΔL of the region of interest after the tissue is deformed, the anisotropy parameter of the tissue may also be obtained.

Figure 7:
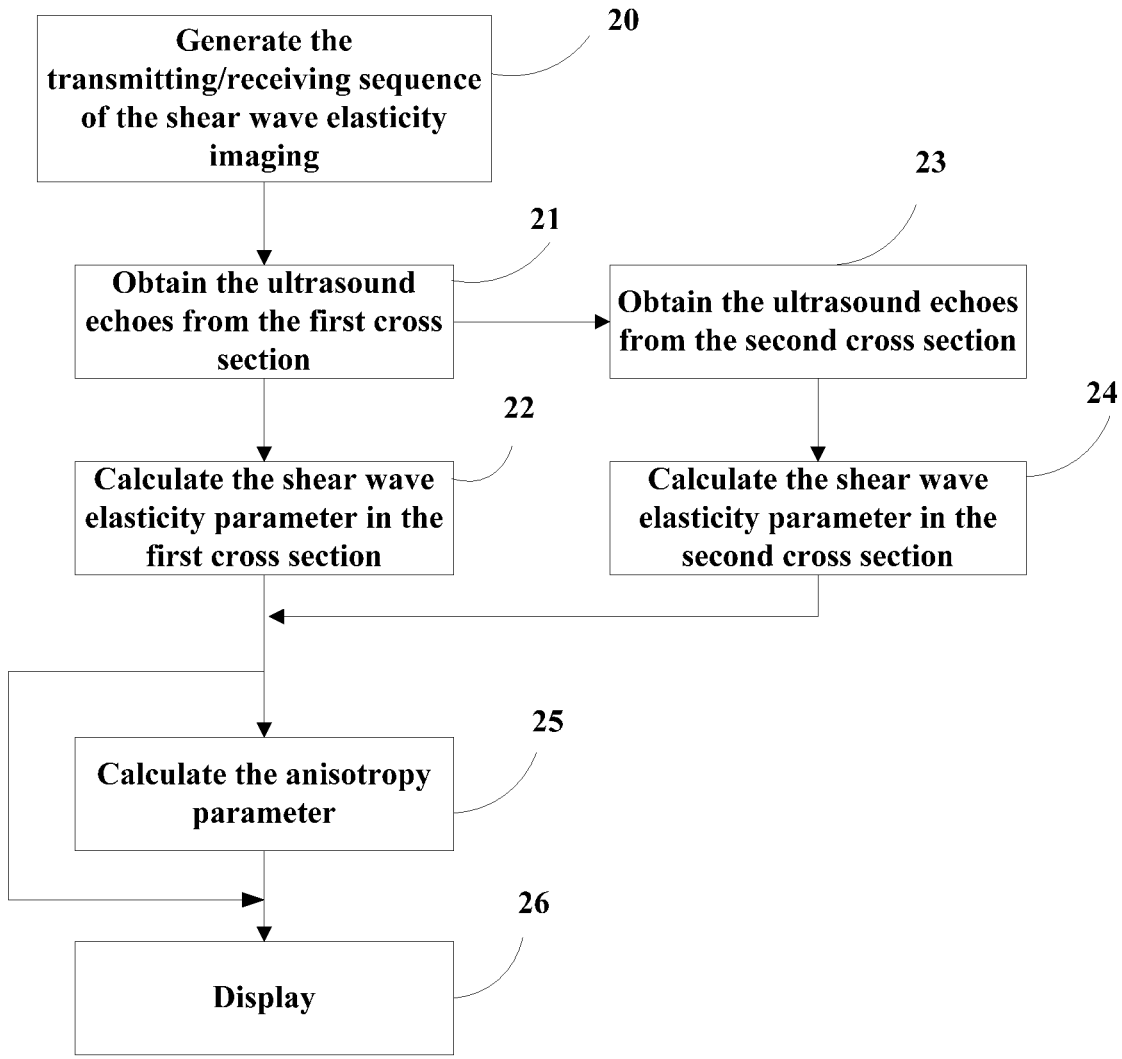
FIG. 7 is a flowchart for calculating the anisotropy parameters in another embodiment.

In other embodiments, the ultrasound probe may generate shear waves propagating in at least two different directions simultaneously or sequentially in the same region of interest in the biological tissue, and transmitting ultrasound waves for detecting the shear waves which will propagate in at least two different cross sections. The ultrasound elasticity measuring device 100 may detect the shear wave elasticity parameter of different cross sections, and calculate the anisotropy parameter of the region of interest according to the shear wave elasticity parameter. The shear waves may be generated in various ways. For example, the ultrasound probe may be configured to transmit ultrasound waves (such as ultrasound pulse waves) to the tissue to generate shear waves that propagate laterally inside the tissue. Alternatively, the ultrasound probe may be configured to impact the tissue to generate shear waves that propagate longitudinally inside the tissue. The processing flow of this embodiment may be shown in FIG. 7 and include the following steps.

In step 20, the acoustic radiation force may be generated in the biological tissue to deform the biological tissue.

Figure 8:
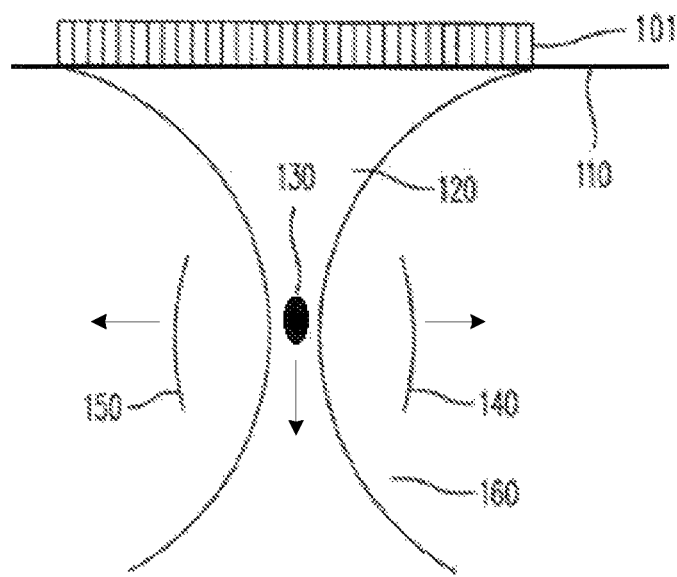
FIG. 8 is a schematic diagram showing the generation of the shear waves by the ultrasound probe.

In the present embodiment, the ultrasound probe may also be configured to transmit pulse waves. When the user places the ultrasound probe on the biological tissue, the ultrasound probe may transmit the pulse wave to the biological tissue. As shown in FIG. 8, the ultrasound probe 101 is closely attached to the surface 110 of the tissue 160. When the pulse waves 120 generated by the ultrasound probe 101 impact the tissue 160, due to the characteristics of the pulse waves, a focus point 130 may be formed in the tissue 160. A displacement along the ultrasound beam direction may occur. Due to the adhesion between tissues, the lateral shear waves 140 and 150 may be formed near the focus point 130. In another embodiment, the shear wave may also be generated by the vibration of the probe driven by a vibrator. This kind of shear wave elasticity imaging is called transient elasticity imaging.

In step 21, the transmitting and receiving sequence of the shear wave elasticity imaging may be generated to control the ultrasound probe to transmit the first ultrasound wave to the biological tissue which may propagate in the first cross section in the biological tissue and receive the echoes of the first ultrasound wave to obtain the first echo signal. In the present embodiment, the shear wave elasticity parameters may be used to calculate the anisotropy parameters. Therefore, the transmitting and receiving sequence may be the same as the transmitting and receiving sequence for performing the shear wave elasticity imaging. For example, in addition to the transducer parameters for the transmitting and the general parameters of the transmitted ultrasound wave, the transmitting sequence may further include the depth, focus position and duration, etc. of the transmitted ultrasound wave, and the receiving sequence may include the transducer parameters, the receiving angle and depth, etc.

When the shear waves are generated, the transmitting/receiving sequence control module may control the ultrasound probe to transmit the ultrasound waves to the region of interest of the tissue. The ultrasound waves scan the first cross section of the region of interest. The ultrasound probe may receive the echoes from the first cross section to obtain the first echo signal.

In step 22, the shear wave elasticity parameter of the region of interest in the first cross section may be calculated according to the first echo signal corresponding to the first cross section, which may be the first elasticity result. The shear wave elasticity parameter may be the shear wave propagation velocity, the Young's modulus or the shear modulus.

Figure 9:
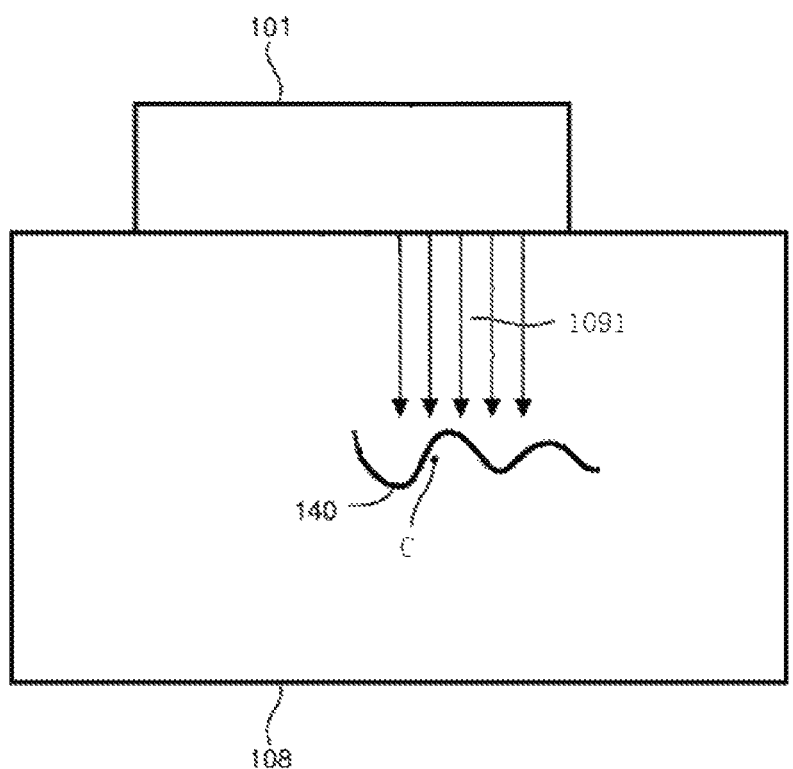
FIG. 9 is a schematic diagram of detecting the shear waves.

The data processing module may calculate the displacement of the portion of the tissue at a set depth within a period of time during the propagation of the shear wave according to the received echo signal. As shown in FIG. 9, the path of the shear wave may be in the first cross section 1091. Through the detection to point C, it may be determined whether the shear wave has reached the point C. When the displacement of the point C is maximum, it may be determined that the shear wave 140 reaches the point C. Alternatively, when the velocity of the point C is the fastest, it may be determined that the shear wave 140 reaches the point C. Alternatively, when the phase of the movement of the point C reaches a certain value, it may be determined that the shear wave reaches this point. Various methods may be used to calculate the propagation velocity of the shear wave. For example, the propagation path or trajectory of the shear wave may be determined by the time when the shear wave 140 reaches the point C, and the shear wave trajectory map may be drawn. According to the trajectory of the shear wave, the slope of the points on the propagation path of the shear wave may be obtained. The slope may be the propagation velocity of the shear wave.

For an isotropic elastomer, there is an approximate relationship between the shear wave propagation velocity and the Young's modulus and shear modulus as the following:

$$E=3\rho c^2=3G$$

Where, c represents the shear wave velocity, ρ represents the tissue density, E represents the Young's modulus of the tissue, and G represents the shear modulus of the tissue. Generally, the value of ρ may be the density of water. Therefore, when the shear wave propagation velocity is obtained, other elasticity related parameters may be further calculated, such as the Young's modulus and the shear modulus, etc.

In step 23, the ultrasound echoes from the second cross section may be obtained. The cross section may be changed using the same method as those in the step 13 of the embodiment above, to obtain the ultrasound echoes from the second cross section. When the biological tissue is deformed, the ultrasound probe may be configured to transmit the second ultrasound wave to the region of interest which may propagate in the second cross section in the biological tissue and receive the echoes of the second ultrasound wave to obtain the second echo signal corresponding to the second cross section.

In the case that the manual adjustment is used, when the user complete the adjustment and place the ultrasound probe on the biological tissue, the shear wave propagating in the tissue may be generated by transmitting pulse waves to the tissue or impacting the tissue with the probe, and the transmitting/receiving sequence control module may control the ultrasound probe to transmit the ultrasound wave to the region of interest in the tissue. The ultrasound wave may scan the second cross section of the region of interest. The ultrasound probe may receive the ultrasound echoes from the second cross section.

When the automatic adjustment is used, the ultrasound waves propagating in the first and second cross sections may be generated for the same shear wave, or for two different shear waves. The two different shear waves may be generated simultaneously or at different time. For example, in one embodiment, a first ultrasound beam may be transmitted to the biological tissue to deform the biological tissue, and the ultrasound probe may be configured to transmit the first ultrasound wave mentioned above to the region of interest to obtain the first echo signal. A second ultrasound beam may be transmitted to the biological tissue to deform the biological tissue, and the ultrasound probe may be configured to transmit the second ultrasound wave mentioned above to the region of interest to obtain the second echo signal. The first ultrasound beam and the second ultrasound beam may be focused at different positions in the biological tissue or may generate different shear waves in the biological tissue. The first ultrasound beam transmitted to the biological tissue may generate a first shear wave in the biological tissue, and the ultrasound probe may be configured to transmit the first ultrasound wave mentioned above to the region of interest through which the first shear wave passes, thereby obtaining the first echo signal. The second ultrasound beam transmitted to the biological tissue may generate a second shear wave in the biological tissue, and the ultrasound probe may be configured to transmit the second ultrasound wave mentioned above to the region of interest through which the second shear wave passes, thereby obtaining the second echo signal. Here, the propagation directions of the first shear wave and the second shear wave may be the same or different. The region of interest through which the first shear wave passes and the region of interest through which the second shear wave passes may be the same region of interest. In one embodiment, the ultrasound probe may generate shear waves propagating in at least two different directions in the same region of interest in the biological tissue, and transmit ultrasound waves for detecting the shear waves, thereby obtaining ultrasound waves scanning at least two different cross sections. Regarding how to obtain the first ultrasound wave and the second ultrasound wave propagating in two different cross sections, reference may be made to the description above. The first shear wave and the second shear wave may be generated simultaneously or successively.

In step 24, the shear wave elasticity parameter of the region of interest in the second cross section may be calculated according to the second ultrasound echo signal corresponding to the second cross section, which may be the second elasticity result. Regarding the calculation process of the second elasticity result, reference may be made to the description about step 22 above. The first elasticity result and the second elasticity result may be directly output to the display module for display, such as be displayed on the same display interface so as to facilitate the comparison of the elasticity results of the two sections by the doctor. In the present embodiment, step 25 may also be performed.

In step 25, the anisotropy parameter may be calculated. The data processing module may calculate the anisotropy parameter according to the shear wave elasticity parameter N1 of the region of interest in the first cross section and the shear wave elasticity parameter N2 of the region of interest in the second cross section. The anisotropy parameter may be the difference between N1 and N2, the ratio of N1 and N2, or other functions of the difference or the ratio.

In step 26, the first elasticity result and the second elasticity result calculated according to the first echo signal and the second echo signal may be output. For example, the results may be displayed. For example, the elasticity calculation results may be output through the display module. For example, in some embodiments, the data processing module may perform at least one of the following in response to the calculation of the elasticity results:

(1) outputting a first elasticity distribution may according to the first elasticity result, and outputting a second elasticity distribution map according to the second elasticity result; and (2) outputting the anisotropy parameters according to the first elasticity result and the second elasticity result, such as displaying the anisotropy parameters calculated according to the first elasticity result and the second elasticity result. Regarding the step 26, reference may be made to the step 15 described above.

In one embodiment, the ultrasound probe may generate the shear wave in the biological tissue to detect the elasticity result of the region of interest, and the calculated elasticity result may be the shear wave elasticity parameter of the region of interest. The shear wave elasticity parameter may be the shear wave propagation velocity, the Young's modulus or the shear modulus.

In some embodiments, the data processing module may also output the shear wave elasticity parameter of the region of interest in a certain cross section to the display module for display, and at the same time display the anisotropy parameter of the region of interest. They may be displayed by texts, numbers and/or graphs.

In some embodiments, the user may select multiple regions of interest, and the ultrasound elasticity measuring device may calculate the anisotropy parameters of the multiple regions of interest with the methods above. These anisotropy parameters may be displayed in a comparative manner. Alternatively, an anisotropy parameter distribution map of the multiple regions of interest may be displayed.

For the one-dimensional ultrasound probe, each time the elasticity parameter in one cross section is detected, the tissue may be deformed once. For the matrix or three-dimensional ultrasound probe, it can detect the elasticity parameters of each section, the tissue may be deformed once for the detection of the elasticity parameter in each cross section. However, it may also be possible that, after the tissue is deformed for one time, the ultrasound waves propagating in different cross sections may be generated by the transmitting sequence and the receiving sequence generated by the transmitting/receiving sequence control module, so as to receive the ultrasound echoes from the different cross sections. Therefore, it will not necessary to generate the deformation in the tissue for multiple times.

In the embodiments above, for convenience of understanding, two different cross sections are used as examples for description. Those skilled in the art should understand that it may also be possible to calculate the anisotropy parameter of the region of interest according to the ultrasound echo signals from more cross sections of the same region of interest.

Furthermore, in some embodiments, other methods may also be used to obtain the elasticity measurement results. For example, nuclear magnetic resonance MR may also be used to obtain the elasticity distribution or the elasticity results by adjusting the measurement direction or section. For example, in one embodiment, an elasticity comparative measuring method is provided, which may include the following steps.

In step A1, the echo signals from the first cross section in the region of interest may be obtained, and the first elasticity result corresponding to the region of interest may be calculated according to the echo signals from the first cross section.

In step A2, the echo signals from the second cross section in the region of interest may be obtained, and the second elasticity result corresponding to the region of interest may be calculated according to the echo signals from the second cross section.

In step A3, the anisotropy parameter of the region of interest may be calculated according to the first elasticity result and the second elasticity result.

In step A4, in response to the calculation of the elasticity result, at least one of the following may be performed:
(1) outputting the first elasticity distribution map according to the first elasticity result, and outputting the second elasticity distribution map according to the second elasticity result; and
(2) displaying the anisotropy parameter according to the first elasticity result and the second elasticity result.

In step A3, the anisotropy parameter may include a secondary statistics based on the first elasticity result and the second elasticity result. For example, the anisotropy parameter may include at least one of the ratio of the first elasticity result and the second elasticity result, the difference between the first elasticity result and the second elasticity result and a function of the ratio of or difference between the first elasticity result and the second elasticity result, etc. The function of the ratio of or difference between the first elasticity result and the second elasticity result may be the square or the third power of the ratio or difference, etc.

In the present embodiment, the elasticity distribution map may be an elasticity distribution map formed by mapping the elasticity results corresponding to the various location points in the region of interest to the spatial positions in the region of interest.

Regarding the step A1, reference may be made to the description about the steps 10 to 12 or the description about the steps 20 to 22 above. Regarding the step A2, reference may be made to the description about the steps 13 to 14 or the description about the steps 23 to 24.

According to the embodiments of the present disclosure, when the ultrasound device enters the multi-section examination mode (such as the tissue anisotropy measurement mode or the elasticity comparison mode) through the user operation, the system may process the ultrasound echo signals from two different cross sections manually scanned by the user with the ultrasound probe or selected by the user through the buttons or the touch screen to obtain the elasticity results of the two cross sections. Alternatively, the elasticity results of more cross sections may be obtained, and then two of the elasticity results may be selected. Thereafter, the system may perform an associating processing on the elasticity results of the two cross sections so as to facilitate the comparison of the elasticity results of the two cross sections. The associating processing may be, for example, displaying the elasticity results of the two cross sections on the same screen, so that the user can understand the elasticity results of two different cross sections by observing on the same screen, where the elasticity results may be images, values, texts, or graphs. The associating processing may also be performing a calculation on the elasticity results of two cross sections and then outputting the anisotropy parameter.

According to the description above with respect to the methods or devices/apparatuses, it can be understood that the anisotropy parameter corresponding to each region of interest may be obtained according to the first elasticity result and the second elasticity result corresponding to each region of interest. When there are multiple regions of interest, multiple anisotropy parameters corresponding to the multiple regions of interest may be correspondingly obtained. Therefore, in one embodiment, the multiple anisotropy parameters may be output, where each anisotropy parameter may correspond to a region of interest. For example, the system may calculate the anisotropy parameters of different target areas (the target area may include multiple regions of interest) as needed, and comparatively display the anisotropy parameters of the different regions of interest in the target area, or generate an anisotropy parameter distribution map in the multiple regions of interest. For another example, in one embodiment, according to the spatial position distribution of the multiple regions of interest, the anisotropy parameters corresponding to the multiple regions of interest may be mapped to the same coordinate system to obtain the distribution map of the anisotropy parameters corresponding to the multiple regions of interest, which then may be displayed.

In addition, the transmitting/receiving module mentioned above may be configured to control the ultrasound probe to transmit the first ultrasound wave to the region of interest when the biological tissue is deformed, and receive the echoes of the first ultrasound wave to obtain the first echo signal; and control the ultrasound probe to transmit the second ultrasound wave to the region of interest when the biological tissue is deformed, and receive the echoes of the second ultrasound wave to obtain the second echo signal. The data processing module may be configured to calculate the first elasticity result and the second elasticity result, and may also be configured to calculate the elasticity distribution map and the anisotropy parameter. The transmitting/receiving sequence control module (102), the echo processing module (104), the transmitting/receiving module (103) and the data processing module (105) may be integrated on the same board or multiple boards. Alternatively, part or all of the transmitting/receiving sequence control module (102), the echo processing module (104), the transmitting/receiving module (103) and the data processing module (105) may be implemented in one or more processes.

The functions involved in the present disclosure may be implemented either by the program described in the above embodiments or by hardware, such as a dedicated integrated circuit built by gate circuits. Those skilled in the art will understand that various programs in the embodiments above may be stored in a computer-readable storage medium, and the storage medium may include a read-only memory, a random access memory, a magnetic disk, or an optical disk, etc. The data processing module may implement the functions above by executing the program.

Specific examples have been described above to illustrate the present disclosure, which are only used to facilitate the understanding to the present disclosure, but not intended to limit the present disclosure. For those skilled in the art, several simple deductions, modifications or replacements may be made according to the concepts of the present disclosure.

The invention claimed is:

1. An elasticity comparative measuring method, comprising:

when a biological tissue is deformed by using an ultrasound probe, controlling, via a processor, the ultrasound probe to transmit a first ultrasound wave in a first transmitting plane to a region of interest in the biological tissue and a second ultrasound wave in a second transmitting plane intersecting with the first transmitting plane to the region of interest by controlling a time delay using a transmitting sequence, the first ultrasound wave propagating in a first cross section along a direction of muscle fibers in the region of interest and the second ultrasound wave propagating in a second cross section perpendicular to the direction of muscle fibers in the region of interest, wherein the first cross section and the second cross section intersect with each other in the biological tissue from different directions;

receiving, via the ultrasound probe, echoes of the first ultrasound wave to obtain a first echo signal;

receiving, via the ultrasound probe, echoes of the second ultrasound wave to obtain a second echo signal;

obtaining, via the processor, a first elasticity result corresponding to the first cross section along the direction of muscle fibers in the region of interest according to the first echo signal;

obtaining, via the processor, a second elasticity result corresponding to the second cross section perpendicular to the direction of muscle fibers in the region of interest according to the second echo signal; and outputting, via a display, the first elasticity result and the second elasticity result, wherein the outputting comprises: calculating an anisotropy parameter according to the first elasticity result and the second elasticity result, and outputting the anisotropy parameter, wherein multiple first elasticity results and multiple second elasticity results are obtained when the biological tissue is deformed, and the method further comprises:

sensing a first pressure when the first elasticity result is obtained each time and a second pressure when the second elasticity result is obtained each time; and normalizing the obtained multiple first elasticity results by using the first pressures sensed at different times to obtain a normalized first elasticity result, and normalizing the obtained multiple second elasticity results by using the second pressures sensed at different times to obtain a normalized second elasticity result.

2. The method of claim 1, wherein outputting the first elasticity result and the second elasticity result further comprises:

outputting a first elasticity distribution map according to the first elasticity result and a second elasticity distribution map according to the second elasticity result.

3. The method of claim 2, wherein the anisotropy parameter comprises a secondary statistic based on the first elasticity result and the second elasticity result, and the anisotropy parameter includes a comparative analysis result of elasticity results obtained in different cross sections.

4. The method of claim 1, wherein the anisotropy parameter comprises at least one of a ratio of the first elasticity result and the second elasticity result, a difference between the first elasticity result and the second elasticity result, and a function of the ratio of or the difference between the first elasticity result and the second elasticity result.

5. The method of claim 1, wherein the biological tissue is deformed by one or more of a vibration caused by an external force, an ultrasound sound radiation force, or pressing with the ultrasound probe.

6. The method of claim 1, wherein:

controlling the ultrasound probe to transmit the first ultrasound wave in the first transmitting plane to the region of interest in the biological tissue comprises:

transmitting a first ultrasound beam to the biological tissue to generate a first shear wave in the biological tissue, and controlling the ultrasound probe to transmit the first ultrasound wave in the first transmitting plane to the region of interest through which the first shear wave passes;

and controlling the ultrasound probe to transmit the second ultrasound wave in the second transmitting plane intersecting with the first transmitting plane to the region of interest comprises:

transmitting a second ultrasound beam to the biological tissue to generate a second shear wave in the biological tissue, and controlling the ultrasound probe to transmit the second ultrasound wave in the second transmitting plane intersecting with the first transmitting plane to the region of interest through which the second shear wave passes;

wherein the region of interest through which the first shear wave passes is the same region of interest through which the second shear wave passes.

7. The method of claim 1, wherein:

the first elasticity result comprises a first length change; and the second elasticity result comprises a second length change different from the first length change.

8. The method of claim 1, wherein the region of interest comprises multiple regions of interest, and the method further comprises: obtaining the anisotropy parameter corresponding to each of the multiple regions of interest according to the first elasticity result and the second elasticity result corresponding to each of the multiple regions of interest, respectively obtaining multiple anisotropy parameters corresponding to the multiple regions of interest, and outputting the multiple anisotropy parameters.

9. The method of claim 8, wherein outputting the multiple anisotropy parameters comprises:

mapping the multiple anisotropy parameters corresponding to the multiple regions of interest to a same coordinate system according to a spatial position distribution of the multiple regions of interest to obtain an anisotropy parameter distribution map corresponding to the multiple regions of interest.

10. An elasticity measuring device, comprising:

an ultrasound probe configured to transmit ultrasound waves to a region of interest in a biological tissue and receive echoes of the ultrasound waves; and a processor configured to perform operations including:

when the biological tissue is deformed by using the ultrasound probe, controlling the ultrasound probe to transmit a first ultrasound wave in a first transmitting plane to the region of interest and a second ultrasound wave in a second transmitting plane intersecting with the first transmitting plane to the region of interest by controlling a time delay using a transmitting sequence, the first ultrasound wave propagating in a first cross section along a direction of muscle fibers in the region of interest and the second ultrasound wave propagating in a second cross section perpendicular to the direction of muscle fibers in the region of interest, wherein the first cross section and the second cross section intersect with each other in the biological tissue from different directions;

controlling the ultrasound probe to receive echoes of the first ultrasound wave to obtain a first echo signal;

controlling the ultrasound probe to receive echoes of the second ultrasound wave to obtain a second echo signal;

obtaining a first elasticity result corresponding to the first cross section along the direction of muscle fibers in the region of interest according to the first echo signal obtaining a second elasticity result corresponding to the second cross section perpendicular to the direction of muscle fibers in the region of interest according to the second echo signal; and outputting the first elasticity result and the second elasticity result through a display, wherein the outputting comprises: calculating an anisotropy parameter according to the first elasticity result and the second elasticity result, and outputting the anisotropy parameter, wherein multiple first elasticity results and multiple second elasticity results are obtained when the biological tissue is deformed, and the processor is further configured to perform operations including:

controlling a pressure sensor to sense a first pressure when the first elasticity result is obtained each time and a second pressure when the second elasticity result is obtained each time; and normalizing the obtained multiple first elasticity results by using the first pressures sensed at different times to obtain a normalized first elasticity result, and normalizing the obtained multiple second elasticity results by using the second pressures sensed at different times to obtain a normalized second elasticity result.

11. The device of claim 10, wherein outputting the first elasticity result and the second elasticity result further comprises:

outputting a first elasticity distribution map according to the first elasticity result and a second elasticity distribution map according to the second elasticity result.

12. The device of claim 10, wherein:

controlling the ultrasound probe to transmit the first ultrasound wave in the first transmitting plane to the region of interest in the biological tissue comprises:

transmitting a first ultrasound beam to the biological tissue to generate a first shear wave in the biological tissue, and controlling the ultrasound probe to transmit the first ultrasound wave in the first transmitting plane to the region of interest through which the first shear wave passes;

and controlling the ultrasound probe to transmit the second ultrasound wave in the second transmitting plane intersecting with the first transmitting plane to the region of interest comprises:

transmitting a second ultrasound beam to the biological tissue to generate a second shear wave in the biological tissue, and controlling the ultrasound probe to transmit the second ultrasound wave in the second transmitting plane intersecting with the first transmitting plane to the region of interest through which the second shear wave passes;

wherein the region of interest through which the first shear wave passes is the same region of interest through which the second shear wave passes.

13. The device of claim 10, wherein:

the first elasticity result comprises a first length change; and the second elasticity result comprises a second length change different from the first length change.

14. The device of claim 10, wherein the region of interest comprises multiple regions of interest, and the operations further comprise: obtaining the anisotropy parameter corresponding to each of the multiple regions of interest according to the first elasticity result and the second elasticity result corresponding to each of the multiple regions of interest, respectively obtaining multiple anisotropy parameters corresponding to the multiple regions of interest, and outputting the multiple anisotropy parameters.

* * * * *